United States Patent [19]

Nukada

[11] Patent Number: 5,856,596
[45] Date of Patent: Jan. 5, 1999

[54] PROCESS FOR PREPARING MONO-IODINATED AROMATIC COMPOUND

[75] Inventor: Katsumi Nukada, Ashigara, Japan

[73] Assignee: Fuji Xerox Co., Ltd., Tokyo, Japan

[21] Appl. No.: 907,968

[22] Filed: Aug. 11, 1997

Related U.S. Application Data

[63] Continuation of Ser. No. 391,177, Feb. 21, 1995, abandoned.

[30] Foreign Application Priority Data

Feb. 23, 1994 [JP] Japan .................................. 6-48004

[51] Int. Cl.⁶ .................................................. C07C 17/12
[52] U.S. Cl. .............................................................. 570/206
[58] Field of Search ............................................... 570/206

[56] References Cited

U.S. PATENT DOCUMENTS

| | | | |
|---|---|---|---|
| 3,180,730 | 4/1965 | Klupfel et al. . | |
| 4,240,987 | 12/1980 | Martin et al. ........................... | 570/206 |
| 4,554,360 | 11/1985 | Yamazaki et al. ....................... | 549/261 |

FOREIGN PATENT DOCUMENTS

| | | |
|---|---|---|
| B-34-5466 | 6/1956 | Japan . |
| B-37-16096 | 4/1959 | Japan . |
| A-58-198043 | 11/1983 | Japan . |
| A-63-314554 | 12/1988 | Japan . |
| A-1-280763 | 11/1989 | Japan . |
| A-2-178666 | 7/1990 | Japan . |
| A-2-178667 | 7/1990 | Japan . |
| A-2-178668 | 7/1990 | Japan . |
| A-2-178669 | 7/1990 | Japan . |
| A-2-178670 | 7/1990 | Japan . |
| A-2-190862 | 7/1990 | Japan . |
| A-2-190863 | 7/1990 | Japan . |
| A-2-230255 | 9/1990 | Japan . |
| A-3-78755 | 4/1991 | Japan . |
| A-3-78756 | 4/1991 | Japan . |
| A-3-78757 | 4/1991 | Japan . |
| A-3-114058 | 5/1991 | Japan . |
| A-4-133064 | 5/1992 | Japan . |
| A-4-193852 | 7/1992 | Japan . |
| A-4-312558 | 11/1992 | Japan . |
| A-5-19509 | 1/1993 | Japan . |
| A-5-80550 | 4/1993 | Japan . |
| A-5-313386 | 11/1993 | Japan . |

OTHER PUBLICATIONS

*Ann.*, Bd. 634, (1960), pp. 84–105, Herman O. Wirth et al.
*J. Chemical Society of Japan*, 92 (1971), pp. 1021–1023, Hitomi Suzuki et al.
*Bull. Soc. Chim.*, T.7 (1940), pp. 634–638, P. Rumpf.

*Primary Examiner*—Peter O'Sullivan
*Attorney, Agent, or Firm*—Oliff & Berridge PLC

[57] ABSTRACT

A process for preparing mono-iodinated aromatic compound is disclosed, wherein the process comprises iodinating an aromatic compound, at least two portions of which can be iodinated, in a solvent mixture of water and acetic acid using iodic acid or periodic acid and iodine, wherein the iodic acid or periodic acid and iodine, and the aromatic compound are added in an amount so that the ratio of the atom number of iodine atom to the molecular number of the aromatic compound is less than 1.

The process provides a mono-iodinated aromatic compound having high purity in a high yield.

15 Claims, 1 Drawing Sheet

PROCESS FOR PREPARING MONO-IODINATED AROMATIC COMPOUND

This is a Continuation of application Ser. No. 08/391,177, filed Feb. 21, 1995, now abandoned.

FIELD OF THE INVENTION

The present invention relates to a process for preparing a mono-iodinated aromatic compound having high purity with high yield.

BACKGROUND OF THE INVENTION

Recently, an electrophotographic organic photosensitive material having laminated layer comprising a charge generating layer and a charge transporting layer has been developed.

As a charge transporting material used for a charge transporting layer, various compounds such as pyrazoline compounds as disclosed in JP-B-37-16096 (the term "JP-B" as used herein means an "examined Japanese patent publication"), triarylamine compounds as disclosed in U.S. Pat. No. 3,180,730, stilbene compounds disclosed in JP-A-58-198043 (the term "JP-A" as used herein means an "unexamined published Japanese patent application"), hydrazone compounds as disclosed in JP-B-55-42380, oxadiazole compounds as disclosed in JP-B-34-5466, butadiene compounds as disclosed in JP-A-63-314554, etc., are known.

In these compounds, triarylamine compounds have been particularly noticed in view of high charge-transporting ability (mobility) and recently, various triarylamine compounds are proposed, e.g., in JP-A-1-280763, JP-A-2-178666, JP-A-2-178667, JP-A-2-178668, JP-A-2-178669, JP-A-2-178670, JP-A-2-190862, JP-A-2-190863, JP-A-2-230255, JP-A-3-78755, JP-A-3-78756, JP-A-3-78757, JP-A-3-114058, JP-A-4-133064, JP-A-4-193852, JP-A-4-312558, JP-A-5-19509, JP-A-5-80550, and JP-A-5-313386.

The triarylamine compounds can be synthesized by coupling reaction of an arylamine compound with arylhalide using a copper catalyst generally known. The arylhalide includes aryl bromide or aryl iodide. Of them aryl iodide is preferably used, since an aryl bromide shows a greatly low reactivity in the coupling (tertiary amine formation) reaction in the final stage.

These iodides of aromatic compounds can be synthesized by iodinating an aromatic compound with a sulfuric acid catalyst in a mixed solvent of water and acetic acid using iodic acid and iodine as shown in *Ann.*, 634, 84(1960); by iodinating an aromatic compound with a sulfuric acid catalyst in a mixed solvent of water and acetic acid using periodic acid and iodine as shown in *J. Chemical Society of Japan*, 92, 1021(1971); or by a Sandmeyer reaction using a corresponding amino compound as shown in *Bull. Soc. Chim.*, 7, 634(1940).

In the preparation of biphenylamine compounds disclosed in JP-A-1-280763, terphenylamine compounds disclosed in JP-A-2-190862, pyrenylamine compounds disclosed in JP-A-2-190863, fluorenylamine compounds disclosed in JP-A-2-230255, monoiodobiphenyl, monoiodoterphenyl, monoiodopyrene, or monoiodofluorene is used as an intermediate compound, which are synthesized by the same methods as described above. However, in synthesizing them by the Sandmeyer reaction, the corresponding amino compound which has a very strong toxicity has to be used, although the formation of a diiodo compound can be prevented. Whereby the compound must be treated with a specific care; the treatment after the reaction is complicated; and the yield of the compound is low, such a method being undesirable.

On the other hand, an iodination reaction with iodic acid or periodic acid is carried out with easy but the selectivity in a reaction to form a monoiodo compound or a diiodo compound is low, and thus the reaction product results in comprising a mixture thereof. When the amination reaction is carried out using the mixture containing the monoiodo compound and the diiodo compound, the reaction product after amination also comprises a mixture. Since impurities in the product provide harmful influences on the electrical characteristics of the charge transport material, a purification of the product is required. The molecular weight of these impurities is, however, considerably large not to be purified by distillation, etc., and thus a very expensive purification method such as a column purification, etc., must be used. In addition of expensiveness of iodine, a method accompanied by a formation of many diiodo compounds leads to a costly process in preparing arylamine compound.

Also, since in monoiodo compound and diiodo compound, the solubility of diiodo compound is greatly low, the diiodo compound can not be removed from the product by recrystallization which is simple in the industrial operation and has a large merit in cost. Therefore, for the product which contains about 10% or more of the diiodo compound, purification by distillation is required.

On the other hand, monoiodo compound has a high boiling point and a high melting point, and thus a high vacuum is required in the distillation of monoiodo compound, and the substance obtained by distillation is apt to be solidify to become difficult in handling. When the substance to be subjected to distillation contains a large amount of diiodo compound, in splashes to result in mixing of diiodo compound into the distilled substance by only a single distillation. Thereby, the purity of the product subjected to the single distillation is lowered. In this way, a fractional distillation is required in a purification of the product containing a large amount of diiodo compound, which causes complicated operation and excessive cost.

Also, it is described in *Ann.*, 634, 84(1960) that by carrying out the iodination reaction in a saturated solution of an aromatic compound, the selectivity of monoiodo compound formation is increased. The method, however, does not provide a product having sufficient purity as a raw material used for a charge transporting material at low cost. Any process which will suffice for the above-described needs has not been found until now. The present invention is provided to solve the problems described above.

SUMMARY OF THE INVENTION

The object of the present invention is to provide a process for preparing a mono-iodinated aromatic compound having high purity with high yield and at low cost.

Further, the object of the present invention is to provide a process for preparing a mono-iodinated aromatic compound without using an amino compound having strong toxicity and without carrying out distillation of monoiodo compound, the distillation of monoiodo compound being costly.

Furthermore, the object of the present invention is to provide a process for preparing a mono-iodinated aromatic compound which is useful as an intermediate for preparing a charge transporting amino compound.

As the result of various investigation of iodination reaction of aromatic compound by iodic acid or periodic acid and iodine in a solvent mixture of water and acetic acid, it has been found that by defining the ratio of the atom number of the total iodine atom and the molecule number of the aromatic compound being less than 1, preferably less than 0.8, and more preferably less than 0.5 and the lowest ratio thereof being preferably 0.2, monoiodinated product of the aromatic compound having high purity is obtained.

Also, it has been found that by increasing the ratio of water in the solvent mixture of water and acetic acid, the formation ration of the monoiodinated product is increased and thereby monoiodinated product having high purity is obtained by only recrystallization.

It has also been found that by combining recrystallization with distillation, the monoiodinated product having a further higher purity is obtained with high yield.

The above and other objects and advantages of the present invention are accomplished by a process for preparing mono-iodinated aromatic compound of the present invention.

DETAILED DESCRIPTION OF THE INVENTION

Figure 1:
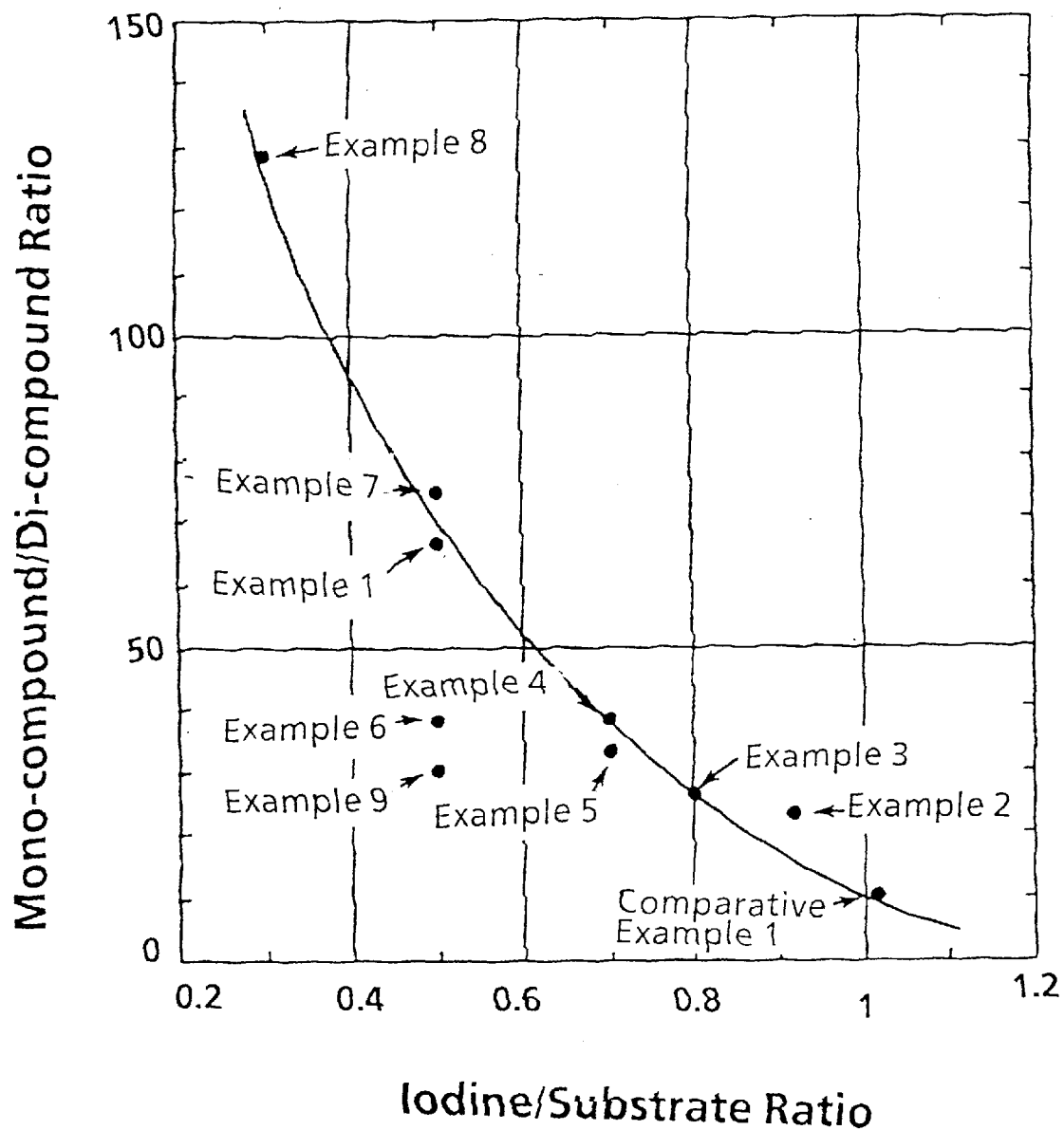
FIG. 1 is a graph showing the relation of the iodine/substrate ratio and the mono-compound/di-compound ratio.

The present invention is described in detail.

The iodination reaction in this invention is carried out by adding definite amount of iodic acid or periodic acid, iodine, an aromatic compound, and, optionally, a catalyst to a solvent mixture of water and acetic acid, and thereafter, stirring the mixture under heating. The solvent mixture of water and acetic acid is used in an amount of 1 to 100 ml per gram of the aromatic compound. If the amount of the solvent mixture is too small, the reaction is reluctant in smooth proceeding and if the amount thereof is too large, the post-treatment is troublesome. Thus, the addition amount of the solvent mixture is preferably in an amount of 2 to 30 ml per gram of the aromatic compound.

The aromatic compound at least two portions of which can be iodinated includes a compound to which two or more of iodine atoms can be substituted in the same molecule. The aromatic compound includes one having two or more of aryl groups, and forming symmetrical structure to a bonding chain connecting the aryl groups. In the symmetrical structure, when an aromatic group is substituted by an iodine atom, the other aromatic group is liable to be substituted by an iodine atom.

The aromatic compound of the present invention includes biphenyl, terphenyl, pyrene, fluorene, etc., which may be substituted by methyl group, ethyl group, fluorine atom, etc.

In the solvent mixture of water and acetic acid, acetic acid is preferably used in an amount of 0.5 to 100 ml per ml of water. If the proportion of water is too large, the organic compound is indissoluble in the solvent mixture and the reaction becomes reluctant to proceed. Also, if the proportion of water is too small, the solubility of the iodinated aromatic compound becomes high and iodination is liable to occur. Thus, in the ratio of water and acetic acid, acetic acid is more preferably used in an amount of 0.5 to 10 ml, and more preferably in an amount of 0.8 to 5 ml per ml, of water.

Iodic acid or periodic acid is allowed to oxidize hydrogen iodide formed by the reaction to proceed smooth reaction. The molar ration of iodic acid to iodine is 1/2.5 or more and the molar ration of periodic acid to iodine is 1/3.5 or more.

Periodic acid can be used in a form of dihydrate or an aqueous solution thereof but in view of safety, it is preferred to use periodic acid in a form aqueous solution.

As the catalyst which may be used for the reaction, an inorganic acid such as sulfuric acid, nitrosylsulfuric acid, an inorganic mixture of sulfuric acid and nitric acid, etc.; an organic acid such as p-toluenesulfonic acid, etc.; or a peroxide such as peracetate, sodium persulfate, etc., is used but sulfuric acid is preferred since sulfuric acid is inexpensive and a side reaction such as a nitration, etc., does not occur when it is used as a catalyst. The catalyst is preferably used in an amount of 0.01 parts by weight or more, and more preferably 0.1 parts by weight or more based on one part by weight of the aromatic hydrocarbon compound.

The reaction is carried out by stirring under heating. The reaction is preferably carried out under heating at a temperature of 80° C. or more, and preferably 80° C. to 100° C., while refluxing the solvent vapor to prevent deposition of iodine, since iodine has a sublimating property and deposits on the upper portion of the reaction vessel. The end of the reaction is confirmed by vanishing of the color of iodine.

After the conclusion of the reaction, the reaction mixture obtained is allowed to be cooled to room temperature and the product obtained is separated. The separated product is dissolved in a proper organic solvent such as methylene chloride, toluene, ethyl acetate, etc. The organic phase thus formed is washed with a diluted aqueous solution of sodium thiosulfate, a diluted aqueous solution of sodium carbonate, etc., and subjected to sufficient washing with water, drying, and the distillation of the solvent. Then, the residue formed is recrystallized from a proper organic solvent. As the organic solvent for the recrystallization, ethyl acetate, toluene, ethanol, etc., are used singly or as a mixture thereof. In particular, ethyl acetate, toluene, a solvent mixture of ethyl acetate and ethanol, or a solvent mixture of toluene and ethanol is preferred. By the recrystallization, monoiodinated aromatic compound having high purity is obtained.

Any organic solvent can be used for the recrystallization in an optional amount. Furthermore, prior to the recrystallization, the monoiodinated aromatic compound having a higher purity can be obtained by purifying the monoiodinated aromatic compound by a distillation.

By distillation of only excessed amount of unreacted aromatic compound, followed by recrystallization, the raw material can be recycled, and while, monoiodinated aromatic compound having high purity can be obtained without distillation of the high-boiling monoiodinated aromatic compound.

The following examples are provided for illustrative purposes only and are in no way intended to limit the scope of the present invention.

Example 1

In a 100 ml flask were placed 18.32 g (119 mmoles) of biphenyl, 50 ml of glacial acetic acid, 50 ml of distilled water, 3.2 ml of concentrated sulfuric acid, 6.26 g (24.7 mmoles) of iodine, and 2.30 g (10.0 m moles) of periodic acid dihydrate and the reaction was carried out in an oil bath at a bath temperature of about 105° C. for 4 hours. After vanishing the iodine color, the reaction mixture was cooled to room temperature to deposite crystals, which were collected by filtration and dissolved in about 50 ml of methylene chloride, and after washing the solution with a diluted aqueous solution of $Na_2S_2O_3$, a diluted aqueous solution of $Na_2CO_3$, and then distilled water, the product was dried.

The purity of the product was determined by HPLC (High Performance Liquid Chromatograph), Biphenyl/4-iodobiphenyl/4,4'-diiodibiphenyl=38.62%/60.47%/0.91%.

Column: Inertsil ODS 5 μm, 4.6×250 mm.

Solvent: MeOH-100%

Flow rate: 1.5 ml/minute

Detection wavelength: 254 nm

In the condition, the ratio of the iodine atoms to the molecule number of the aromatic compound reacted each other (hereinafter, the ratio is referred to as iodine/substrate (aromatic compound) ratio for simplicity) was 59.4 mmoles/ 119 mmoles=0.5.

Also, as an indicator of the reaction selectivity for the monoiodination and the diiodination, the ratio of 4-iodobiphenyl/4,4'-diiodibiohenyl (hereinafter, the ratio is referred to as mono-compound/di-compound ratio for simplicity) was used. The results are shown in Table 1 below. Also, the relation of the iodine/substrate ratio and the mono-compound/di-compound ratio is shown in FIG. 1.

Examples 2 to 9 and Comparative Example 1

By following the same procedure as Example 1 except that the amounts of biphenyl, glacial acetic acid, and distilled water were changed as shown in Table 1 below, the products were obtained and the purity of each product was determined. The results are shown in Table 1. Also, the relation of iodine/substrate ratio and mono-compound/di-compound ratio is shown in FIG. 1.

TABLE 1

| Sample | Biphenyl (g) | Biphenyl I/Sub. ratio | Solvent Acetic acid (ml) | Water (ml) | A.a./- water ratio | Mono- C/di-C ratio |
|---|---|---|---|---|---|---|
| 1 | 18.32 | 0.5 | 50 | 50 | 1 | 66.5 |
| 2 | 10.0 | 0.917 | 80 | 80 | 1 | 23.4 |
| 3 | 11.45 | 0.8 | 25 | 25 | 1 | 26.3 |
| 4 | 13.09 | 0.7 | 40 | 40 | 1 | 38.0 |
| 5 | 13.09 | 0.7 | 25 | 25 | 1 | 33.0 |
| 6 | 18.32 | 0.5 | 70 | 17.5 | 4 | 38.3 |
| 7 | 18.32 | 0.5 | 25 | 25 | 1 | 74.9 |
| 8 | 30.54 | 0.3 | 25 | 25 | 1 | 128.7 |
| 9 | 18.32 | 0.5 | 90 | 10 | 9 | 30.5 |
| C-1 | 9.0 | 1.015 | 80 | 20 | 4 | 10.3 |

I/sub. ratio: Iodine/substrate ratio
A.a./water ratio: Acetic acid/water ratio
Mono-C/di-C ratio: Mono-compound/di-compound ratio
Sample 1 to 9: Samples of the examples of this invention
C-1: Sample of Comparative Example 1

Example 10 (Purification Method 1)

The mixture obtained in Example 1 was recrystallized with a solvent mixture of 10 ml of ethyl acetate and 5 ml of ethanol to provide 10.78 g of 4-iodobiphenyl (yield 64.8%, biphenyl/4-iodobiphenyl/4,4'-diiosobiphenyl=3.56%/ 95.67%/0.77%). Further, by recrystallizing the product with a solvent mixture of 10 ml of ethyl acetate and 5 ml of ethanol, 8.09 g of 4-iodobiphenyl (yield 48.6%, biphenyl/ 4-iodobiphenyl/4,4'-diiodobiphenyl=0.15%/99.7%/0.11%) was obtained. The purification method such as in Example 10, wherein the purification is carried out by only recrystallization, but by no distillation, is designated Purification Method 1.

Example 11 (Purification Method 2)

After carrying out the same reaction procedure as in Example 1, excessive biphenyl was distilled off under reduced pressure (at about 100° C. and at 0.55 mm Hg) and the residue was recrystallized with a solvent mixture of 10 ml of ethyl acetate and 5 ml of ethanol to provide 11.26 g of 4-iodobiphenyl (yield 67.6%, biphenyl/4-iodobiphenyl/4,4'- diiodibiphenyl=0.34%/99.06%/0.60%). The purification method such as in Example 11, wherein after purifying the monoiodinated aromatic compound by distillation under reduced pressure, the residue is purified by recrystallization, is designated Purification Method 2.

Example 12 (Purification method 3)

After carrying out the same reaction procedure as in Example 1, 4-iodobiphenyl obtained was purified by distillation under reduced pressure (at about 140° C. and at 0.21 mm Hg) and further recrystallization with a solvent mixture of 10 ml of ethyl acetate and 5 ml of ethanol to provide 12.50 g of 4-iodobiphenyl (yield 75.0%, biphenyl/4-iodobiphenyl/ 4,4'-diiodobiphenyl=0.10%/99.9%/0.0%). The purification method of the example, wherein the purification method such as in Example 12, wherein after purifying the monoiodinated aromatic compound formed by distillation under reduced pressure, the product is further purified by recrystallization, is designated Purification Method 3.

Comparative Example 2

The mixture obtained by the same manner as in Comparative Example 1 was purified by the Purification Method 1. The mono-compound/di-compound ratio after the purification was 9.8, which showed that the ratio of 4,4'-diiodibiphenyl was rather increased.

Comparative Example 3

The mixture obtained by the same manner as in Comparative Example 1 was purified by the same method as the Purification Method 3. The mono-compound/di-compound ratio after the purification was 242.7 (yield 63.3%, biphenyl/ 4-iodobiphenyl/4,4'-diiodobiphenyl=0.08%/99.51%/ 0.41%). That is, since the content of 4,4'-diioidobiphenyl after the reaction is large, by carrying out the Purification Method 3 similarly, 4,4-diiodobiphenyl is still mixed in the purified product.

Application Example 1

In a 50 ml three-neck flask were placed 4.9 g of 3,3',4, 4'-tetradiphenylamine, 6.0 g of 4-iodobiphenyl obtained in Example 11, 3.0 g of anhydrous potassium carbonate, 0.2 g of copper sulfate penta-hydrate, and 2 ml of n-tridecane, after carrying out the reaction for 23 hours at 220° C. in a nitrogen gas stream, the reaction product was cooled to about 80° C., 50 ml of n-hexane was added to the reaction mixture, the mixture was passed through 35 g of active alumina, furthermore, the active alumina was dissolved off with 250 ml of n-hexane, and the solvent was distilled off under reduced pressure.

The residue was recrystallized with a solvent mixture of ethyl acetate and ethanol to provide 5.9 g of N,N-bis(3,4-dimethylphenyl)-4-biphenylamine (yield 74%, purity 99.6%, m.p.=119° to 120.5° C.). The purity of the product was sufficient for use as a charge transport material.

According to the present invention, a monoiodinated aromatic compound which is an important intermediate for synthesizing a charge transport material for an organic photoreceptor is obtained at high purity, with high yield, and at low cost.

While the invention has been described in detail and with reference to specific embodiments thereof, it will be apparent to one skilled in the art that various changes and modifications can be made therein without departing from the spirit and scope thereof.

What is claimed is:

1. A process for preparing a monoiodinated aromatic compound comprising iodinating an aromatic compound in a solvent mixture of water and acetic acid using iodic acid or periodic acid and iodine, wherein the iodic acid or periodic acid and iodine and the aromatic compound are added in an amount so that the ratio of the atom number of total iodine to the molecular number of the aromatic compound is less than 0.8, and wherein the ratio of acetic acid to water is 0.8 to 5.0 by volume.

2. A process for preparing monoiodinated aromatic compound as claimed in claim 1, wherein after the iodination reaction, the product is purified by distillation.

3. A process for preparing a monoiodinated aromatic compound as claimed in claim 1, wherein after the iodination reaction, the excessive aromatic compound is removed by distillation and the residue is recrystallized to purify the monoiodinated aromatic compound.

4. A process for preparing a monoiodinated aromatic compound as claimed in claim 1, wherein after the iodination reaction, the monoiodinated aromatic compound is purified by recrystallization only.

5. A process for preparing a monoiodinated aromatic compound as claimed in claim 1, wherein the aromatic compound is one having two or more aryl groups and forming a symmetrical structure to a bonding chain therebetween.

6. The process according to claim 1, wherein the ratio of the atom number of total iodine atom and the molecular number of the aromatic compound is less than 0.5.

7. The process according to claim 1, wherein the ratio of the atom number of total iodine atom and the molecular number of the aromatic compound is less than 0.2.

8. The process according to claim 1, wherein the solvent mixture is used in an amount of 1 to 100 ml per gram of the aromatic compound.

9. The process according to claim 1, wherein the solvent mixture is used in an amount of 2 to 30 ml per gram of the aromatic compound.

10. The process according to claim 1, wherein the molar ratio of iodic acid to iodine is 1/2.5.

11. The process according to claim 1, wherein the molar ratio of periodic acid to iodine is 1/3.5.

12. The process according to claim 1, further comprising adding a catalyst selected from the group consisting of sulfuric acid, nitrosylsulfuric acid, a mixture of sulfuric acid and nitric acid, p-toluenesulfonic acid, peracetate and sodium persulfate.

13. The process according to claim 12, wherein the catalyst is used in an amount of at least 0.01 parts by weight based on one part by weight of the aromatic compound.

14. The process according to claim 1, wherein the iodination reaction is carried out at a temperature of greater than or equal to 80° C.

15. The process of claim 14, wherein the iodination reaction is carried out at a temperature between 80° C. and 100° C.

* * * * *